(12) United States Patent
Shafirstein

(10) Patent No.: US 8,858,545 B2
(45) Date of Patent: Oct. 14, 2014

(54) SELECTIVE CONDUCTIVE INTERSTITIAL THERMAL THERAPY DEVICE

(75) Inventor: Gal Shafirstein, Amherst, NY (US)

(73) Assignees: Board of Trustees of the University of Arkansas, Little Rock, AR (US); Arkansas Children's Hospital Research Institute, Inc., Little Rock, AR (US)

( * ) Notice: Subject to any disclaimer, the term of this patent is extended or adjusted under 35 U.S.C. 154(b) by 930 days.

(21) Appl. No.: 12/806,561

(22) Filed: Aug. 16, 2010

(65) Prior Publication Data

US 2010/0318077 A1    Dec. 16, 2010

Related U.S. Application Data

(60) Division of application No. 11/373,710, filed on Mar. 10, 2006, now abandoned, which is a continuation-in-part of application No. 11/028,157, filed on Jan. 3, 2005, now Pat. No. 7,361,173, which is a continuation of application No. 10/336,973, filed on Jan. 6, 2003, now Pat. No. 6,872,203, which is a continuation-in-part of application No. 10/228,482, filed on Aug. 27, 2002, now Pat. No. 6,780,177.

(51) Int. Cl.
*A61B 18/14* (2006.01)
*A61B 18/08* (2006.01)
*A61B 18/24* (2006.01)
*A61B 17/00* (2006.01)
*A61B 18/00* (2006.01)

(52) U.S. Cl.
CPC ....... *A61B 18/24* (2013.01); *A61B 2017/00084* (2013.01); *A61B 18/082* (2013.01); *A61B 2018/00011* (2013.01); *A61B 2017/00101* (2013.01); *A61B 2017/00867* (2013.01)
USPC ................................. 606/28; 606/41; 606/31

(58) Field of Classification Search
USPC ............. 606/27–31, 41; 607/88, 89, 101, 102
See application file for complete search history.

(56) References Cited

U.S. PATENT DOCUMENTS

| 4,646,737 A | 3/1987 | Hussein et al. |
| 4,672,962 A | 6/1987 | Hershenson |
| 4,691,703 A | 9/1987 | Auth et al. |
| 4,735,201 A | 4/1988 | O'Reilly |

(Continued)

OTHER PUBLICATIONS

Neuwirth, R., et al., The Endometrial Ablator: A New Instrument, Obstetrics & Gynecology, vol. 83, No. 5, Part 1, pp. 792-796, May 1994.

(Continued)

*Primary Examiner* — Michael Peffley
(74) *Attorney, Agent, or Firm* — Richard Blakely Glasgow

(57) ABSTRACT

An apparatus and method for thermally destroying tumors. A tip has a plurality of deployable thermal conductive elements whose temperatures are individually controllable. This allows the shape of the thermal field to be controlled and for specific areas to be protected from excessive heat by cooling those specific areas while ablating other areas. In another embodiment, the deployable thermal conductive elements are individually deployable to various lengths to further aid in shaping the thermal field. The temperatures and the shape of the thermal field may be monitored and controlled by a data processing device, such as a microprocessor. Further selectivity in defining the area of tissue to be treated may be achieved by introducing into the tissue thermal additives that alter the thermal properties of the tissue.

19 Claims, 10 Drawing Sheets

(56) References Cited

U.S. PATENT DOCUMENTS

| | | | | |
|---|---|---|---|---|
| 4,844,072 | A | 7/1989 | French et al. | |
| 4,860,744 | A | 8/1989 | Johnson et al. | |
| 4,872,458 | A | 10/1989 | Kanehira et al. | |
| 4,949,718 | A | 8/1990 | Neuwirth et al. | |
| 5,047,025 | A | 9/1991 | Taylor et al. | |
| 5,057,105 | A | 10/1991 | Malone et al. | |
| 5,105,808 | A | 4/1992 | Neuwirth et al. | |
| 5,159,925 | A | 11/1992 | Neuwirth et al. | |
| 5,190,539 | A | 3/1993 | Fletcher et al. | |
| 5,191,883 | A | 3/1993 | Lennox et al. | |
| 5,292,321 | A | 3/1994 | Lee | |
| 5,345,936 | A | 9/1994 | Pomeranz et al. | |
| 5,417,689 | A | 5/1995 | Fine | |
| 5,425,731 | A | 6/1995 | Daniel et al. | |
| 5,456,682 | A | 10/1995 | Edwards et al. | |
| 5,492,529 | A | 2/1996 | Neuwirth et al. | |
| 5,536,267 | A | 7/1996 | Edwards et al. | |
| RE35,330 | E | 9/1996 | Malone et al. | |
| 5,571,153 | A | 11/1996 | Wallsten | |
| 5,586,982 | A | 12/1996 | Abela | |
| 5,672,173 | A * | 9/1997 | Gough et al. | 606/41 |
| 5,683,384 | A | 11/1997 | Gough et al. | |
| 5,728,094 | A | 3/1998 | Edwards | |
| 5,105,808 | B1 | 7/1998 | Neuwirth et al. | |
| 5,810,802 | A | 9/1998 | Panescu et al. | |
| 5,810,804 | A * | 9/1998 | Gough et al. | 606/41 |
| 5,827,269 | A | 10/1998 | Saadat | |
| 4,949,718 | B1 | 11/1998 | Neuwirth et al. | |
| 5,860,974 | A | 1/1999 | Abele | |
| 5,868,740 | A | 2/1999 | LeVeen et al. | |
| 5,879,349 | A * | 3/1999 | Edwards | 606/45 |
| 5,891,134 | A | 4/1999 | Goble et al. | |
| 5,897,552 | A | 4/1999 | Edwards et al. | |
| 5,957,920 | A | 9/1999 | Baker | |
| 6,006,755 | A | 12/1999 | Edwards | |
| 6,024,743 | A | 2/2000 | Edwards | |
| 6,053,912 | A | 4/2000 | Panescu et al. | |
| 6,053,937 | A | 4/2000 | Edwards et al. | |
| 6,056,746 | A | 5/2000 | Goble et al. | |
| 6,071,280 | A | 6/2000 | Edwards et al. | |
| 6,139,570 | A | 10/2000 | Saadat et al. | |
| 6,221,071 | B1 | 4/2001 | Sherry et al. | |
| 6,238,392 | B1 | 5/2001 | Long | |
| 6,258,086 | B1 | 7/2001 | Ashley et al. | |
| 6,290,697 | B1 | 9/2001 | Tu et al. | |
| 6,293,943 | B1 | 9/2001 | Panescu et al. | |
| 6,312,428 | B1 | 11/2001 | Eggers et al. | |
| 6,505,629 | B1 * | 1/2003 | Mikus et al. | 128/898 |
| 6,689,127 | B1 | 2/2004 | Gough et al. | |
| 6,706,037 | B2 * | 3/2004 | Zvuloni et al. | 606/21 |
| 6,780,177 | B2 | 8/2004 | Shafirstein et al. | |
| 6,872,203 | B2 | 3/2005 | Shafirstein et al. | |
| 7,182,761 | B2 | 2/2007 | Garabedian et al. | |
| 7,238,184 | B2 * | 7/2007 | Megerman et al. | 606/41 |
| 7,942,870 | B2 * | 5/2011 | Berzak et al. | 606/21 |
| 2002/0049436 | A1 | 4/2002 | Zvuloni et al. | |
| 2004/0204683 | A1 | 10/2004 | McGuckin, Jr. et al. | |
| 2005/0119645 | A1 | 6/2005 | Shafirstein et al. | |
| 2007/0129714 | A1 * | 6/2007 | Elkins et al. | 606/21 |

OTHER PUBLICATIONS

International Search Report, PCT/US03/20474, Mailing Date Nov. 25, 2003.
Written Opinion, PCT/US03/20474, Mailing Date Apr. 23, 2004.
International Preliminary Examination Report, PCT/US03/20474, Mailing Date Aug. 18, 2004.
International Search Report and Written Opinion, PCT/US07/03426, Mailing Date Nov. 5, 2007.
International Preliminary Report on Patentability, PCT/US07/03426, Mailing Date Sep. 25, 2008.

* cited by examiner

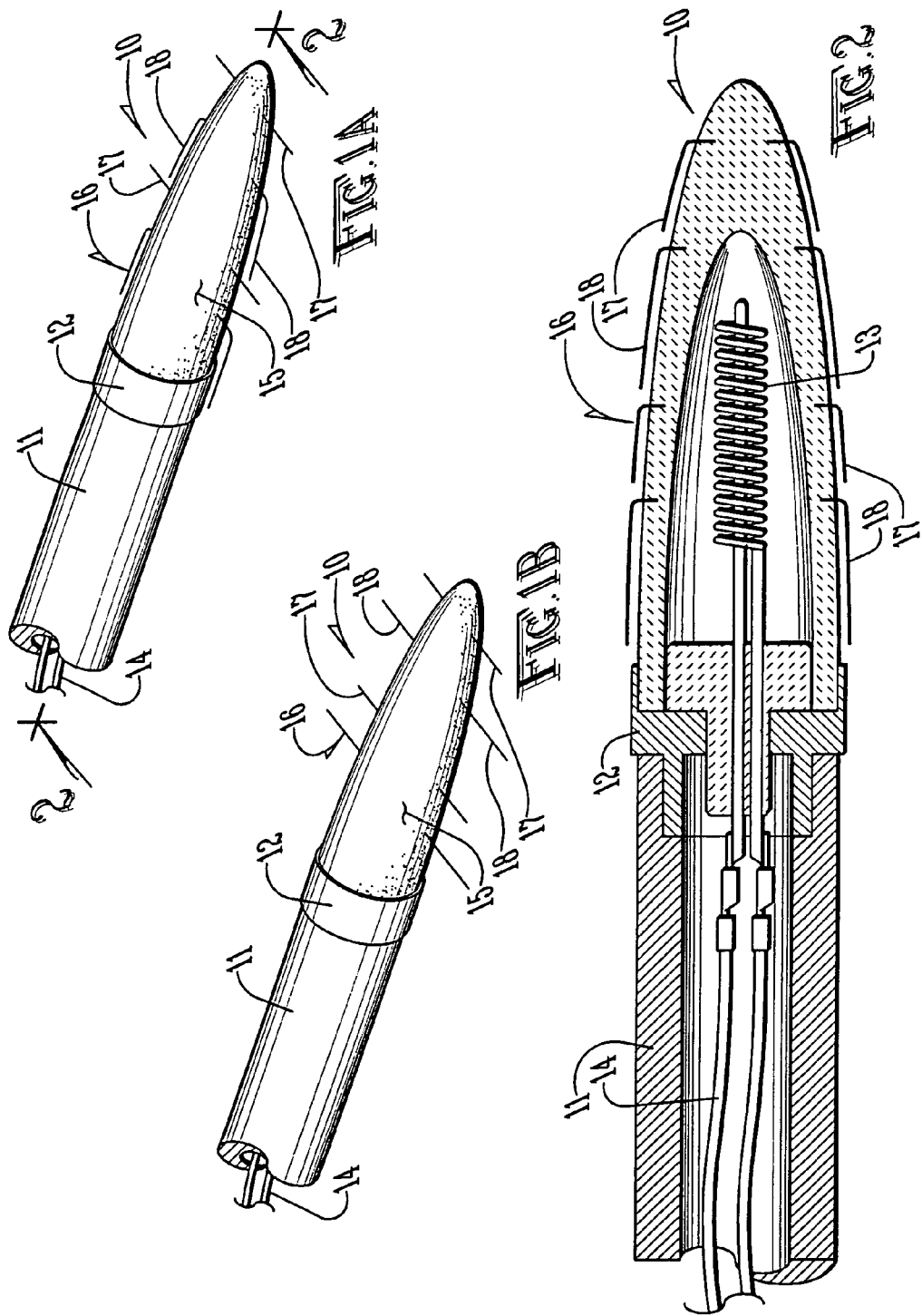

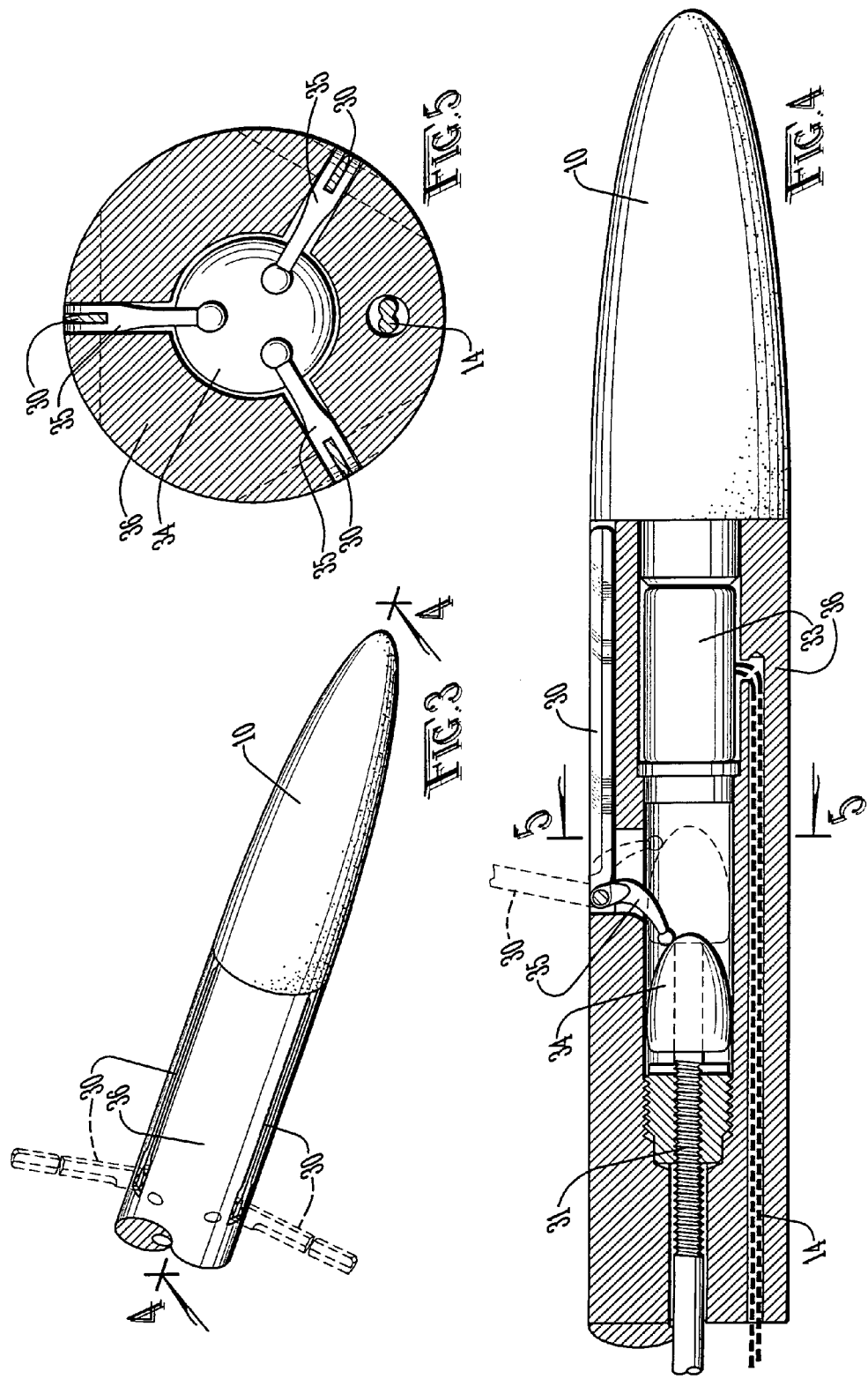

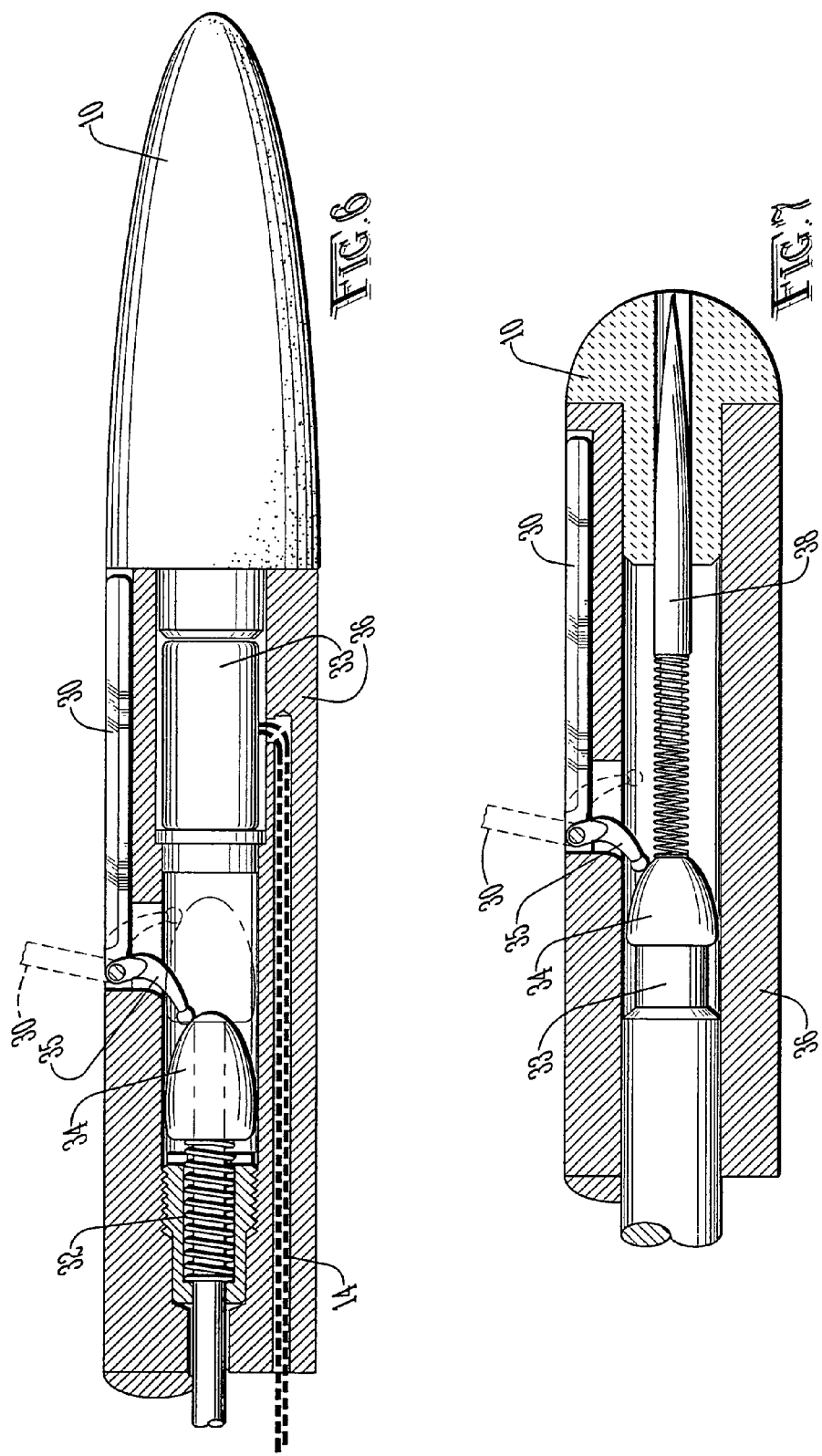

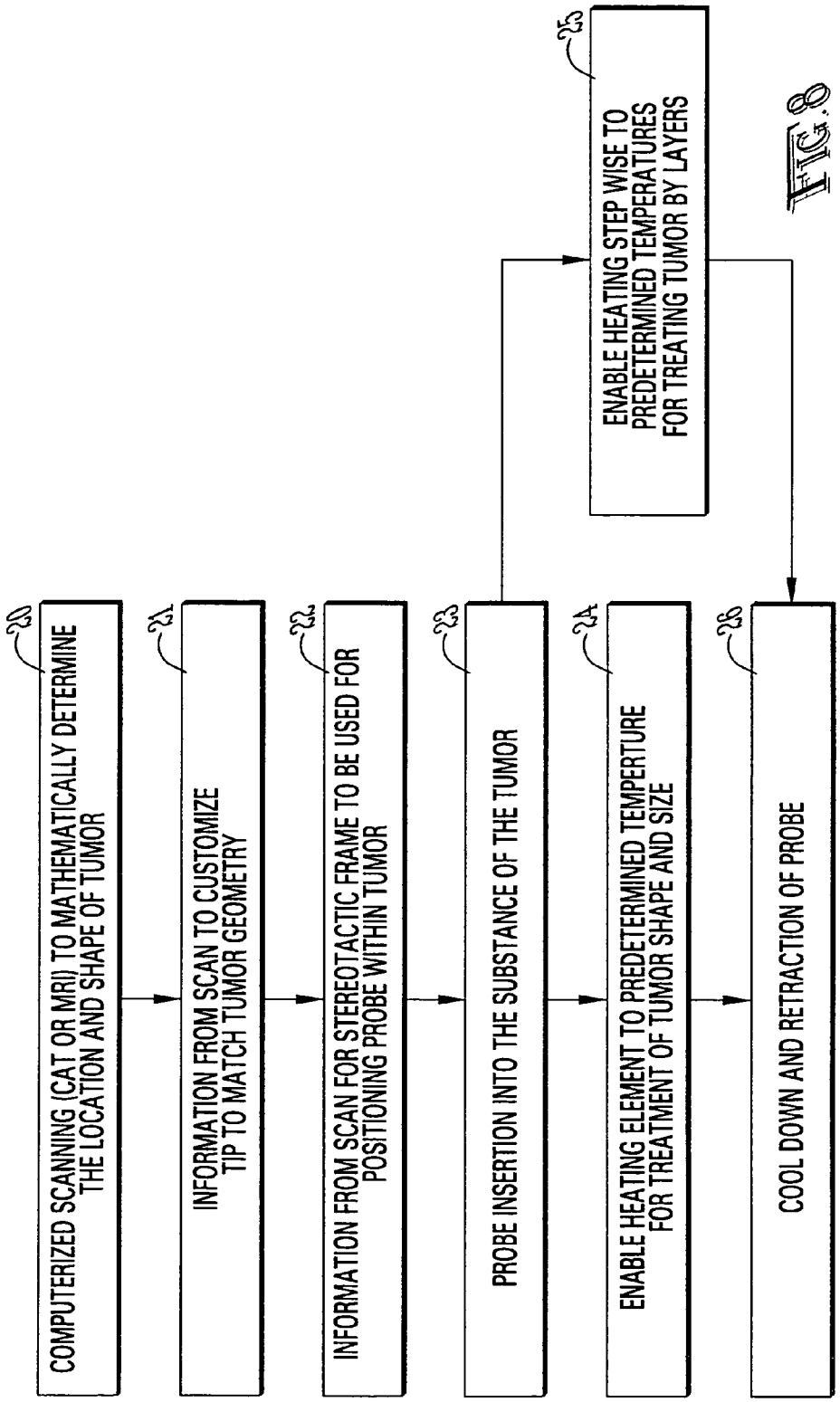

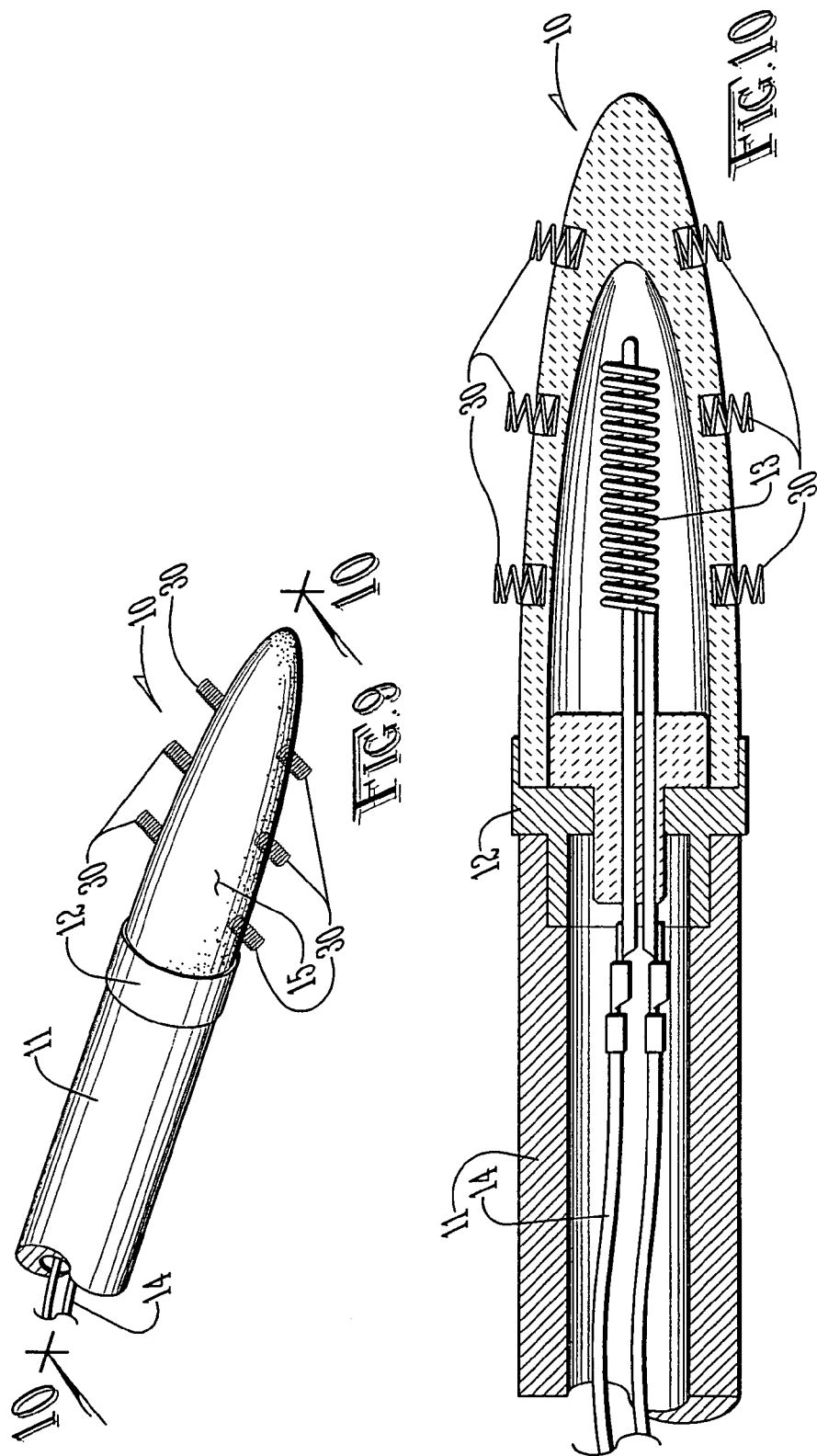

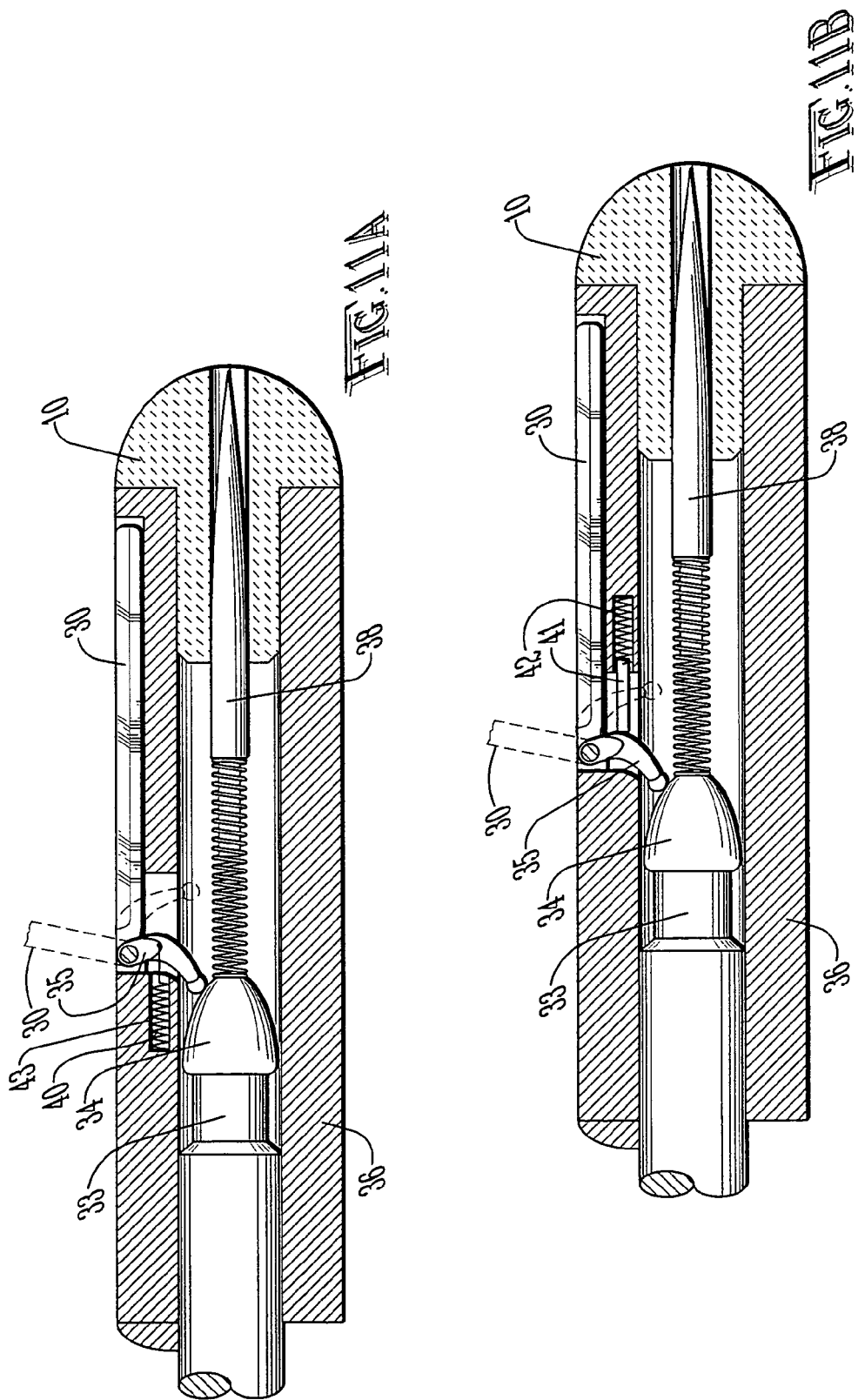

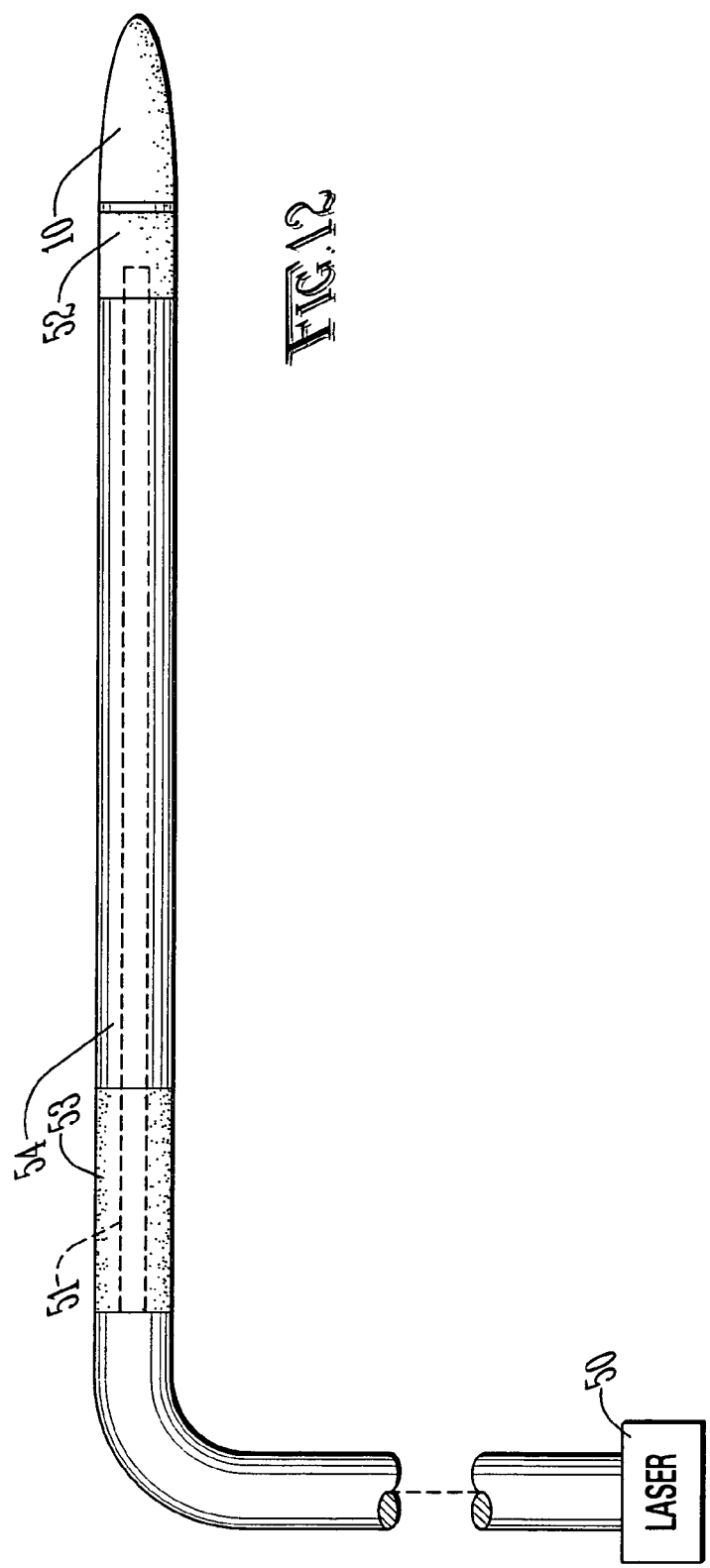

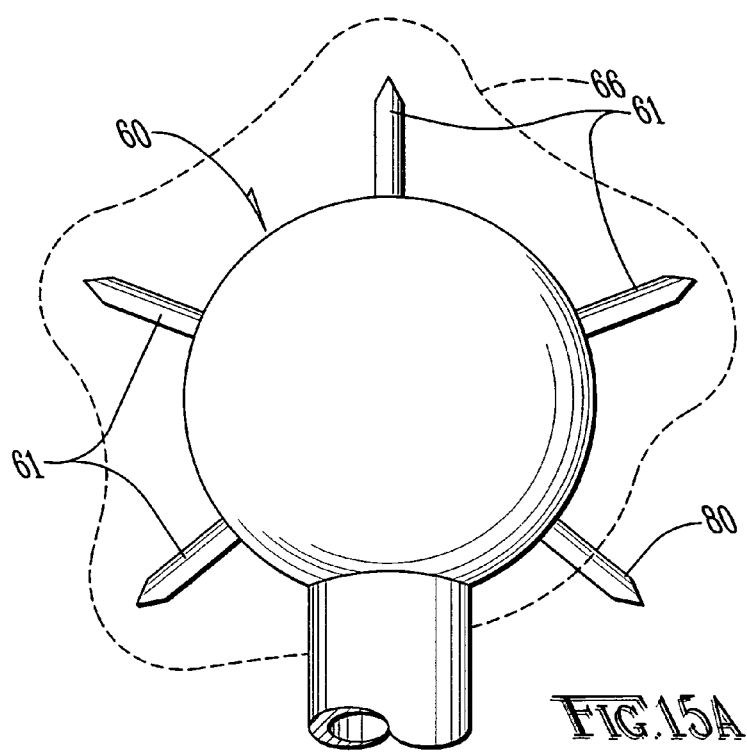
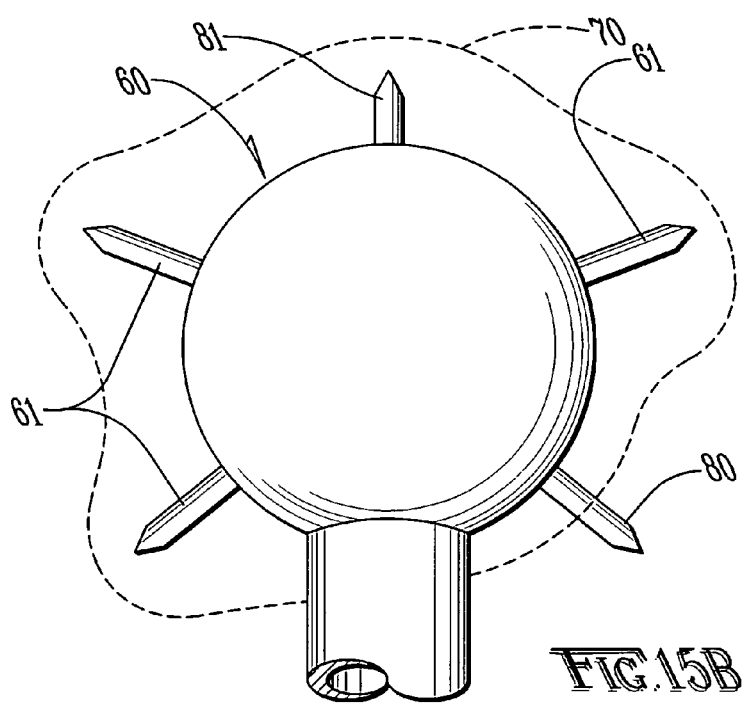

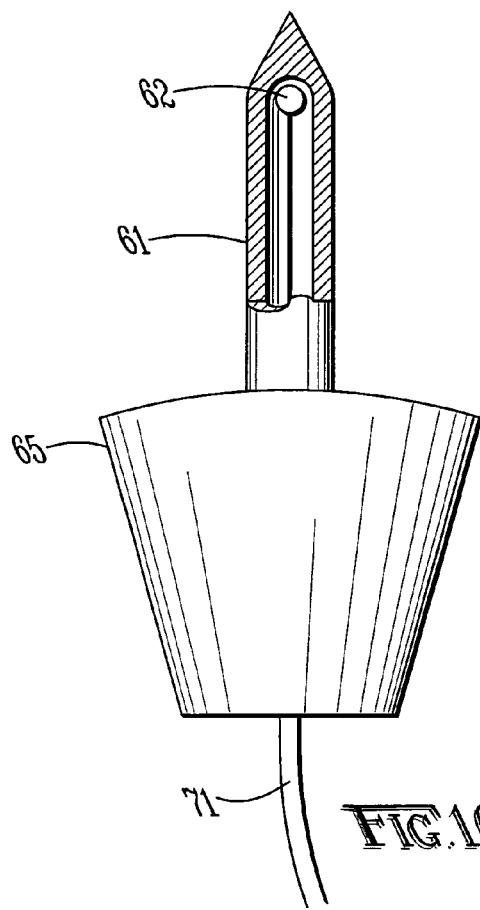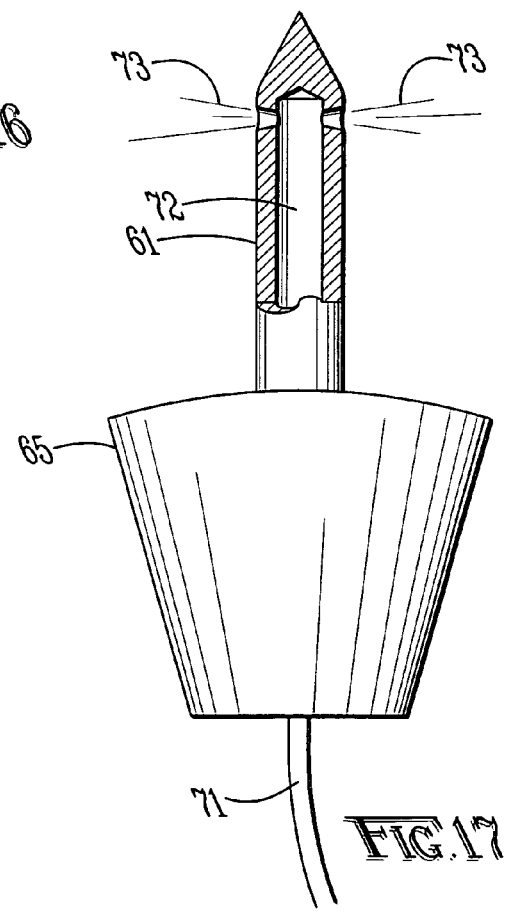

SELECTIVE CONDUCTIVE INTERSTITIAL THERMAL THERAPY DEVICE

CROSS-REFERENCE TO RELATED APPLICATIONS

This application is a divisional of U.S. patent application Ser. No. 11/373,710, filed Mar. 10, 2006, now abandoned, which is a continuation-in-part of U.S. patent application Ser. No. 11/028,157, filed Jan. 3, 2005, now U.S. Pat. No. 7,361,173, which is a continuation of U.S. patent application Ser. No. 10/336,973 filed Jan. 6, 2003, now U.S. Pat. No. 6,872,203, which is a continuation-in-part of U.S. patent application Ser. No. 10/228,482 filed Aug. 27, 2002, now U.S. Pat. No. 6,780,177, all of which are incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to methods and devices for treating body tissues such as tumors or lesions with thermal energy, and in particular, to such methods and devices that deploy thermally conductive elements to treat a predetermined shape of tissue.

2. Brief Description of the Related Art

Within the last ten years, interstitial thermal therapy of tumors has become an accepted method for treating cancerous tumors. These minimally invasive therapeutic procedures are used to kill cancer tumors without damaging healthy tissues surrounding it. Increasing the temperature of the tumor above a threshold level of about 70-130 C will cause tumor death. Interstitial thermal devices for thermal tissue ablation including radio frequency ablation (RFA), microwave and laser based technologies have been developed and have received 510K FDA clearance. All of these techniques use radiation to transfer the energy to the tumor, and therefore the heat in the tumor is generated indirectly through local energy absorption sites (e.g., blood in the case of a laser or fat in the case of RFA) could result in a non-homogenous heating of the tumor. The consequences of a non-uniform heating of the tumor could include incomplete death of the tumor and/or skin burns and injury of healthy tissues or organs. Incomplete tumor death will result in recurrence of multiple small tumors in the treated area.

Moreover, as most of the heat is transfer by radiation (in laser, RFA and microwave), it is very difficult to calculate the temperature distribution without precisely knowing the fine microstructure (down to the cell level) that cannot be predetermined with a non-invasive method. In addition the temperature measurements are also challenging; in these cases, since the probes could be directly heated by the energy sources and will show it's own temperature rather than that of the tissue. For example, in laser or RFA thermocouples may get hot from the source much quicker than tissue (as they absorb RF and laser energy more than tissue) and will show temperatures that are higher than the actual temperature in the lesion. That could result in insufficient heating and if the operator increases the amount of energy delivered to the tumor, an overheating may occur which will result in burning. Another limitation of RFA is that it is not MRI-compatible.

The limitations of the prior art are overcome by the present invention as described below.

BRIEF SUMMARY OF THE INVENTION

The present invention is an alternative to Laser Interstitial Thermal Therapy (LLIT) and RFA, which is used to destroy tumors or lesions through the absorption of radiation by tissue. However, as discussed above, in the LLIT and RFA processes, the temperature cannot be predicted or easily controlled due to the varying light and RF energy absorption properties of different types of tissue. In addition, RFA will interfere with implants (such as pacemakers) and the patient with such implants cannot be treated with RFA.

The present invention also destroys tumors thermally, but the heat is generated directly by heat, such as by electrical resistance heating, conducted to the tissue rather than through the absorption of non-ionized radiation by the tissue. A process of the present invention may involve digital imaging (x-ray, ultrasound) and/or computerized scanning (CAT, CT, PET, or MRI) to mathematically determine the location and shape of the tumor. The information derived from the scan allows a stereotactic frame or other technique such as ultrasound to be used to position a probe within the tumor.

In one embodiment, the probe comprises a thermally conductive tip containing an electrical resistance heating element. The thermally conductive tip is mounted on the end of a fiber which is separated from the tip by a heat sink to avoid thermal conduction down the fiber. The fiber contains the electrical power leads and other electrical leads connecting to monitoring devices associated with the tip. The tip is coated with a thin biocompatible coating, such as diamond-like coating, ceramic, polymers and the like, to avoid coagulated tissue sticking to the tip.

The area of tissue treated by the tip is determined by the addition of one or more thin, thermal conductive elements, which may be formed of shape memory material, such as nitinol. The shape memory elements are desirably in the form of thin wires or pins which are folded against the tip at lower temperatures and which deploy at selected higher temperatures. The shape memory elements may be deployed in multiple stages at successively higher temperatures so that successive layers of the tumor are exposed to specific temperatures during treatment. Coagulating the tumor in successive layers is desirable to avoid hemorrhaging. By selecting the number, size and placement of the shape memory elements, tumors of varying sizes and shapes may be treated in a predictable, controllable fashion.

In order to control the process, the tip may also be provided with a miniature thermocouple or the like to provide temperature feedback information to control the temperature of the tip. Through knowledge of the shape and location of the tumor obtained from computerized imaging, the design of the tip and thermal conductive elements, and the temperature feedback information, information can be presented to the operator showing the specific progress of the treatment of a tumor and allowing predictable control of the process.

In alternative embodiments, deployable pivoted razorblades rather than thin wires are employed to conduct the thermal energy to the tumor. The razorblades are deployed mechanically rather than being deployed due to temperature dependent shape memory effects. In one embodiment, a linear actuator, comprising a threaded shaft operated by a motor, deploys the razorblade thermal conductive elements. In another embodiment, a nitinol spring is heated so as to extend and deploy the razorblade elements.

In some embodiments, a pyrolytic graphite element may be used to provide the heat source. Pyrolytic graphite has unique thermal properties in that it acts as a resistor axially but is conductive radially.

In a further embodiment, the deployable razorblades are deployed mechanically by a spring-biased copper conductor that serves a dual function—as a plunger to push deploying arms on the razorblades and also as a conductor for the power supply for the pyrolytic graphite heater element. The plunger is housed in a shaft which is coated with an electrically conductive material, for example, gold, to act as the power return or ground so as to complete the electrical circuit supplying power to the heater element. When the plunger moves forwardly to push the arms on the razorblades, it may also extend a needle which helps to hold the probe in place when the razorblades deploy.

The deployable razorblades may be deployed in stages to treat the tumor layer by layer. The deployment may be triggered at specified temperatures as measured by temperature feedback elements in the probe tip.

The present invention uses thermal conduction, as opposed to radiation absorption, to heat the tumor/lesion volume. Since the thermal properties of tissue are relatively homogenous, the results can be predicted. The shape of the probe tip in the form of the deployable thermal conductive elements may be altered during treatment. The combination of shape and activation temperature can be predetermined for any specific tumor/lesion geometry. This offers the following advantages: highly predictable temperature distribution; larger areas can be effectively treated, in a controlled manner, since the heat is dissipated primarily by conduction; localized carbonization will not result in tunneling and the process is safer than LLIT or RFA; the maximum temperature in the treatment zone will never exceed the temperature at the tip of the probe, and therefore, one can easily control the maximum temperature within the tumor/lesion and adjacent tissues; and temperature may be actively controlled via closed loop feedback system, where the maximum temperatures are measured during the process by placing miniature thermocouples at the end of the thermal probe.

In an alternative embodiment, the tip is provided with a plurality of deployable elements whose temperatures are individually controllable to provide heat to the elements and surrounding tissue. This allows the shape of the thermal field to be controlled and for specific areas to be protected from excessive heat by cooling those specific areas while ablating other areas. Treatment areas can be targeted more effectively and particularly sensitive areas can be protected from ablation. Thus, it is possible to ablate targeted areas of tissue near the chest wall, in the head and neck, liver, pancreas and other regions where portions of the tissue require ablation, but nearby portions must be protected from ablation to avoid life threatening injury. The deployable elements may be heated or cooled by any of various techniques known to those skilled in the art. For example, heat may be supplied from a miniature resistance heating coil in each deployable element. Cooling may be accomplished by Peltier effect devices. Heating and/or cooling may be applied by introducing heated or chilled fluid, either liquid such as water or gas such as argon, to a hollow space within the deployable thermal conductive elements.

The temperature of the thermal conductive elements may be monitored by thermal sensors at the ends of the elements. The thermal sensors may be miniature thermocouples located within the end of each element. The temperatures may be monitored and controlled by a data processing device, such as a microprocessor.

In a further alternative embodiment, the tip is provided with a plurality of deployable elements that are individually deployable to various shapes. The deployable elements remain retracted in the tip during insertion into the tissue to be treated. The tip may be heated by joule heating using a miniature heating coil and/or the individual elements may be separately heated. Each element is individually connected to means for deploying the elements. The deploying means may a direct mechanical connection from the elements to an external mechanical control or the deploying means may be associated with each individual deployable element. Other techniques to deploy the elements to a specified length would be known to those skilled in the art. These technique could include electromechanical or pneumatic means. Other techniques could include the application of temperature to induce a shape change in bimetallic elements. Over- or under-treatment of the tissue may be avoided by deploying the deployable elements to individually predetermined lengths to generate a thermal field that approximates the shape of the spatial volume of the tissue to be treated.

Each deployable element may include its individual temperature and/or shape controller in an associated modular package. The tip may be connected by a hollow fiber to external control devices, such as a microprocessor, mechanical actuator, heating and/or cooling fluid supply, thermal additive supply, and electrical power. Each modular package may be connected via control lines through the hollow fiber to the respective external control devices.

Any number of deployable elements could be used depending upon the application. Although the present invention is not limited thereto, it has been found that eight (8) deployable elements allow the creation of a thermal field that can conform to various shapes of tissues to be treated, for example, spherical, ellipsoidal or oblong. Various sizes and shapes of the tip and the deployable elements may be used to fit various shapes of tissue to be treated. The tip, the deployable elements and the associated temperature and/or shape controllers may be replaceable and disposable.

Further selectivity in defining the area of tissue to be treated may be achieved by introducing into the tissue thermal additives that alter the thermal properties, such as thermal diffusivity, specific heat capacity, density or thermal conductivity, of the tissue. Such additives are known to those skilled in the art and may include carbon particles (from 1 nm to 5000 μm) and metal particles including gold nano-particles. Various chemicals are known in the art that bind selectively to tumor cells or that otherwise accumulate in tumors and that can alter the thermal properties of the tumor. It is also known that glucose will increase the thermal conductivity of a tumor into which it is introduced.

The thermal additives may be introduced into the tissue to be treated by various means, for example, by intralesional injection or by intravenous injection. Further, the deployable elements may be employed to spray such additives onto the tissue during or before treatment. A hollow duct in the deployable element may be connected through control lines in the hollow fiber to a source of the additive. The additive is than sprayed from one or more ports opening into the hollow duct.

These and other features, objects and advantages of the present invention will become better understood from a consideration of the following detailed description of the preferred embodiments and appended claims in conjunction with the drawings as described following.

BRIEF DESCRIPTION OF THE SEVERAL VIEWS OF THE DRAWINGS

FIGS. 1A, 1B and 2 are views of an embodiment of the present invention in which the deployable thermal conductive elements are shape memory wires. FIG. 1A is a perspective view showing the first stage deployment of the shape memory wires. FIG. 1B shows the second stage deployed. FIG. 2 is a sectional view of the device of FIGS. 1A and 1B along the lines 2-2 of FIGS. 1A and 1B with the shape memory wires in the non-deployed configuration.

FIGS. 3-5 are views of an alternative embodiment of the present invention in which the deployable thermal conductive elements are pivoted razorblades deployed by a linear actuator. FIG. 3 is a perspective view of the present invention in which the pivoted razorblades are shown by broken lines in the deployed configuration. FIG. 4 is a sectional view along the line 3-3 of FIG. 3. FIG. 5 is a sectional view along the line 5-5 of FIG. 3.

FIG. 6 is a sectional view of a further alternative embodiment of the present invention in which the deployable thermal conductive elements are pivoted razorblades deployed by a nitinol muscle wire.

FIG. 7 is a sectional view of a further alternative embodiment of the present invention in which the deployable thermal conductive elements are pivoted razorblades deployed by a plunger. The activation of the plunger also deploys a needle through the forward end of the tip.

FIG. 8 is a block diagram of a method of the present invention.

FIGS. 9 and 10 are views of an embodiment of the present invention in which the deployable thermal conductive elements are shape memory wires in the form of coils. FIG. 9 is a perspective view showing the deployment of the shape memory wires. FIG. 10 is a sectional view of the device of FIG. 9 along the lines 10-10 with the shape memory wires in the non-deployed configuration.

FIGS. 11A and 11B are sectional views of an alternative embodiment of the embodiment of FIG. 7 wherein the deployed razorblades are spring biased to aid in retraction of the razorblades from the deployed position. FIG. 11A is an embodiment in which the biasing spring is located to the proximal side of the probe and FIG. 11B is an embodiment in which the biasing spring is located to the distal side of the probe.

FIG. 12 is a schematic view of an embodiment of the invention in which the tip of the device is a metal tip heated by a remote laser through a waveguide.

FIGS. 15A and 15B illustrate a thermal field generate by a probe. FIG. 15A illustrates the situation where some of the thermal conductive element are heated and some cooled. FIG. 15B illustrates the effect on the thermal field of extending the thermal conductive elements to various lengths.

FIG. 16 is a partial cross section of the end of a thermal conductive element showing a miniature thermocouple in the end.

FIG. 17 is a partial cross section of the end of a thermal conductive element showing a hollow duct and ports for spraying thermal additives.

DETAILED DESCRIPTION OF THE INVENTION

Figure 13:
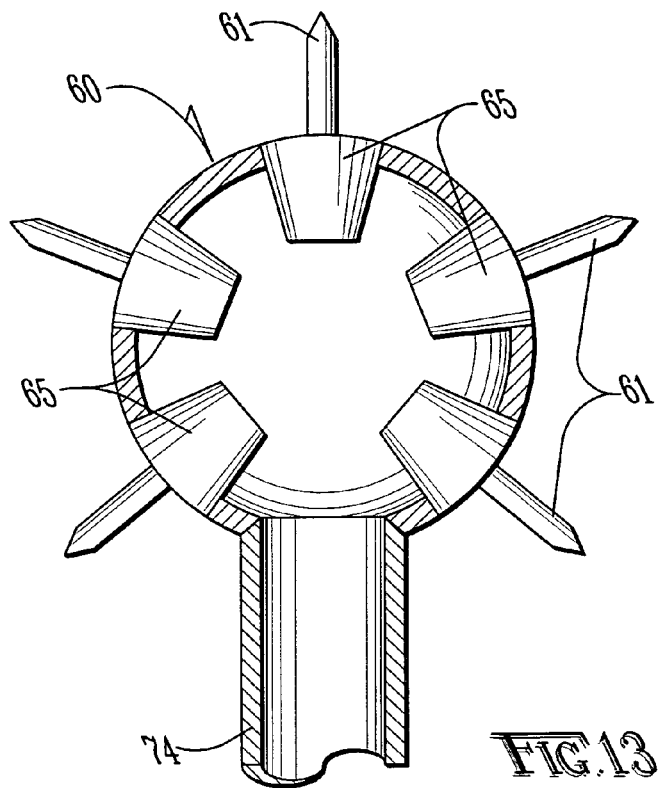
FIG. 13 is a schematic diagram of a cross section of an embodiment of a probe, including a tip, a plurality of deployable thermal conductive elements, and associated temperature and/or length controllers.

With reference to FIGS. 1A-12, the preferred embodiments of the present invention may be described as follows.

The present invention is a miniature thermal apparatus for the controlled destruction of malignant and benign tumors/lesions and abnormal or excess tissue. As used herein, the terms tumors and lesions may be used interchangeably to indicate tissue to be thermally treated by the device and method of the present invention. The present invention comprises a tip 10 mounted onto a fiber 11 that can be inserted through a catheter that has been accurately placed within the tumor/lesion. The tumor/lesion is destroyed via heat generation originating from the specifically designed tip 10 that matches the tumor/lesion geometry. The tip 10 comprises a plurality of deployable thermal conductive elements that may be customized by the number, size and arrangement to be deployable into a geometry that matches the geometry of the tumor/lesion to be thermally treated. The temperature distribution around the tip 10, within the tumor/lesion and in the adjacent tissue may be predicted by mathematical models of the heat transfer equations. Software may be employed in conjunction with the mathematical models of the heat transfer to provide (1) process monitoring and control, (2) custom probe design, and (3) process simulation. Additionally, using this predictive ability, the process may be monitored and controlled with a closed loop feedback system utilizing sensors in the tip 10. The geometry of the tip 10 may be changed as a function of temperature to increase the volume of irreversibly damaged tissue in the tumor/lesion.

As shown in FIG. 8, a process of the present invention involves the step of computerized scanning (CAT, CT, PET, or MRI) to mathematically determine the location and shape of the tumor 20. The information derived from the scan allows the geometry of the tip to be customized to treat the specific shape of the tumor 21 and also allows a stereotactic frame to be used to position the probe within the tumor 22. Ultrasound or the like may be also used to position the probe. The probe is inserted into the tumor 23, and the heating element is activated to a predetermined temperature to treat the tumor 24. Alternatively, the temperature may be increased in a stepwise fashion to treat the tumor in layers 25. Finally, the probe is cooled and withdrawn from the treated tumor 26. As an adjunct to the treatment process, the coagulation of the tumor may be enhanced by the use of a drug effective in reducing bleeding from vascular damage, such as NovoSeven (recombinant factor VIIa) or other coagulant enhancement drug such as Aminocaproic acid (Amicar). NovoSeven is used to stop bleeding in various surgical procedures. The drug is delivered systemically but only works in regions of the body in which vascular damage has taken place. In the procedure of the present invention, the drug would be administered approximately ten minutes prior to the procedure. Thereafter, the apparatus of the present invention is introduced into the tumor. Once the temperature of the tissue has increased to the point that the endothelial cells in the blood vessels are damaged, coagulation is initiated by NovoSeven in the areas of the damaged vessels. The process aids in heat transfer and may aid in the destruction of the tumor by nutrient deprivation. An ancillary advantage to using NovoSeven is that it will decrease the risk of bleeding along the track of the apparatus. The drug is metabolized in about two hours.

The thermally conductive tip 10 contains an electrical resistance heating element 13. The thermally conductive tip 10 is mounted on the end of fiber 11 which is separated from the tip 10 by a heat sink 12 to avoid thermal conduction down the fiber 11. The fiber 11 contains the electrical power leads 14 and may also contain other electrical leads connecting to monitoring devices associated with the tip 10. The tip 10 is coated with a thin biocompatible coating 15 to avoid coagulated tissue sticking to the tip 10. The thin biocompatible coating 15 may be diamond-like coatings, ceramic, polymers and the like.

The area of tissue treated by the tip 10 can be adjusted by the addition of one or more deployable, thermal conductive elements. The deployable elements may be shape memory elements 16 made of shape memory materials, such as nitinol. The shape memory elements 16 are desirably in the form of thin wires or pins which are folded against the tip 10 at lower temperatures as shown in FIG. 2 and which deploy at selected higher temperatures. The shape memory elements 16 may be deployed in multiple stages at successively higher temperatures so that successive layers of the tumor are exposed to specific temperatures during treatment. For example, a set of short shape memory elements 17 may be deployed at a first temperature and a set of longer shape memory elements 18 may be deployed at a higher second temperature. Coagulating the tumor in successive layers is desirable to avoid hemorrhaging. By selecting the number, size and placement of the shape memory elements 16, tumors of varying sizes and shapes may be treated in a predictable, controllable fashion.

In order to control the process, the tip 10 may also be provided with a miniature thermocouple to provide temperature feedback information to control the temperature of the tip 10. Through knowledge of the shape and location of the tumor obtained from computerized imaging, the design of the tip 10 and shape memory elements 16, and the temperature feedback information, information can be presented to the operator showing the specific progress of the treatment of a tumor and allowing predictable control of the process.

As shown in FIGS. 9 and 10, an alternative design of shape memory elements 30 employs shape memory material, such as nitinol, in the form of coils which expand to a deployed configuration as shown in FIG. 9 from a non-deployed configuration as shown in FIG. 10.

Alternative embodiments as shown in FIGS. 3-7 use deployable pivoted razorblades 30 rather than thin shape memory wires as the thermal conductive elements to conduct the thermal energy to the tumor. Desirably, the pivoted razorblades 30 may be made of biocompatible materials, such as composite materials including aluminum silicon carbide, titanium boride and the like. The pivoted razorblades 30 may be deployed mechanically rather than being deployed by a nitinol shape memory wire element. In one embodiment shown in FIG. 4, a linear actuator, comprising a threaded shaft 31 operated by a motor (not shown), deploys the razorblade 30. In another embodiment shown in FIG. 6, a nitinol spring 32 is heated so as to extend and deploy the razorblade elements 30. In both embodiments, a pyrolytic graphite element 33 may be used to provide the heat source. Pyrolytic graphite has unique thermal properties in that it acts as a resistor axially but is conductive radially.

In a further embodiment shown in FIG. 7, the deployable razorblades 30 are deployed mechanically by a spring-biased copper conductor that serves as a plunger 34 to push deploying arms 35 on the razorblades 30. The plunger 34 also acts as a conductor for the power supply for the pyrolytic graphite heater element 33. The copper conductor is housed in a shaft 36 which is coated with an electrically conductive material such as gold to act as the power return or ground so as to complete the electrical circuit supplying power to the heater element 33. When the copper conductor plunger 34 moves forwardly to push the arms 35 on the razorblades 30, it may also extend a needle 36 which helps to hold the probe in place when the razorblades 30 deploy.

FIGS. 11A and 11B are sectional views of an alternative embodiment of the embodiment of FIG. 7 wherein the deployed razorblades 30 are biased by spring 40, 42 to aid in retraction of the razorblades 30 from the deployed position. FIG. 11A is an embodiment in which biasing spring 40 is located to the proximal side of tip 10. Spring 40 is fixed at one end in a bore 43 and at the other end to deploying arm 35. As razorblade 30 is extended, spring 40 also extends and exerts a force tending to retract razorblade 30. FIG. 11B is an embodiment in which the biasing spring 42 is located to the distal side of tip 10. Spring 42 bears against pin 41 which in turn bears against deploying arm 35. As razorblade 30 is deployed, spring 42 is compressed and thereby exerts a force tending to retract razorblade 30. Biasing springs 40, 42 may also be used in the embodiments of FIGS. 4 and 6 as well as FIG. 7.

The device may require increasing the minimum size of the catheter since the tip 10 of the probe may be larger than a standard laser tip.

This limitation is not serious, however. Although the size of the thermal tip 10 is expected to be larger than a standard laser tip, the maximum size could be limited to 1.6-5 mm in diameter, which is still acceptable for interstitial procedures. Also, as shown in FIG. 12, the size of the tip 10 could be reduced to LITT size, by using a laser 50 as an energy source to heat up a metal tip 10.

When using a laser 50 as an energy source, the laser 50 is remotely located from the metal tip 10 and the laser radiation is transmitted through a wave guide fiber 51 to the metal tip 10. The metal tip 10 is desirably stainless steel. The metal tip 10 absorbs the laser radiation and is heated thereby to a high temperature, e.g., 150° C. The heat of the heated metal tip 10 is dissipated to the surrounding tissue through conduction, thereby causing blood coagulation and tissue necrosis around the metal tip 10 in a well defined region. In order to limit the heat flow from the metal tip 10 to the wave guide fiber 51, a heat conductive barrier 52 in the form of insulation or a heat sink may be placed between the metal tip 10 and the wave guide fiber 51. Further, the wave guide fiber 51 may have an insulating jacket 53. The wave guide fiber 51 may also be cooled by cool air flowing through the wave guide fiber 51. A portion of the wave guide fiber 51 adjacent to the metal tip 10 may be in the form of a tube 54 through which the cool air flows. The tube 54 may be formed from a metal, such as copper, a composite material or a ceramic material.

The laser 50 is desirably a $CO_2$ laser. Although there is low absorption (around 9%) of $CO_2$ laser radiation by stainless steel, the amount of energy required to heat stainless steel is low due to the low heat capacity of stainless steel (0.46 $Jgr^{-1} C^{-1}$) compared to blood (3.6 $Jgr^{-1} C^{-1}$). Therefore, a stainless steel metal tip 10 of 1 gram could be heated to high temperatures of up to 300-500° C. by a 50 Watt $CO_2$ laser.

To avoid tissue sticking, the metal tip 10 is desirably coated with a thin layer, e.g., 5 μm, of biocompatible ceramic, such as alumina or titanium nitride, or a biocompatible polymer, such as Teflon®. A ceramic coating may be applied by physical vapor deposition, a standard process in the industry.

Since the heat of the metal tip 10 is dissipated by conduction, the temperature profile can be calculated using known finite difference or finite element methods. Since the thermal properties of all human tissues are similar, accurate temperatures predictions are possible. Since the critical temperatures are not a strong function of time, the irreversible thermal damage of tissues can be controlled through the heating time. To limit necrosis of tissues to a well defined region, the size of the metal tip 10 can be minimized. Deployable thermally conductive elements, as described heretofore, may be added to the metal tip 10 to determine the shape of the thermally treated tissue. Such deployable thermal elements may be deployed in stages.

Figure 14:
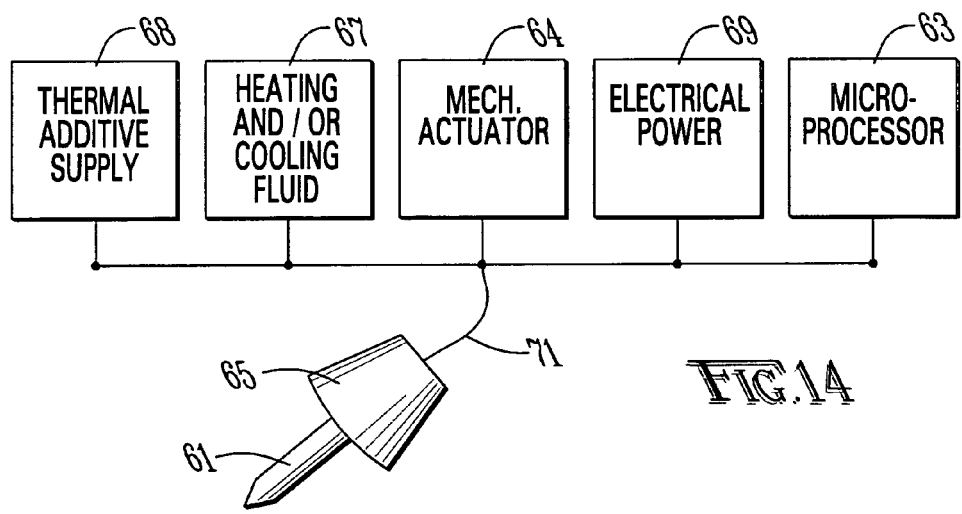
FIG. 14 is a schematic diagram of an individual deployable thermal conductive element and its associated temperature and/or length controller with connections via control lines to external controllers.

With reference to FIGS. 13-17, an alternative embodiment of the present invention is described. In this alternative embodiment, the tip 60 is provided with a plurality of deployable elements 61 with temperature providing means for providing for providing an individually controllable temperature to said each deployable element and its surrounding tissue. This allows the shape of the thermal field 66 to be controlled and for specific areas to be protected from excessive heat by cooling those specific areas while ablating other areas. For example, as shown in FIG. 15A, elements 61 are heated and element 80 is cooled, producing the thermal field 66. Treatment areas can be targeted more effectively and particularly sensitive areas can be protected from ablation. Thus, it is possible to ablate targeted areas of tissue near the chest wall, in the head and neck, liver, pancreas and other regions where portions of the tissue require ablation, but nearby portions must be protected from ablation to avoid life threatening injury. The deployable elements may be heated or cooled by any of various techniques known to those skilled in the art. For example, heat may be supplied from a miniature resistance heating coil in each deployable element. Cooling or heating may be supplied the action of an electromagnetic field, such as Peltier effect devices. Heating and/or cooling may be applied by introducing heated or chilled fluid, either liquid such as water or gas such as argon, to a hollow space (not shown) within the deployable elements 61. Fluids, solids, gases or mixtures of the same at temperatures below the maximum temperature of the probe may be used to cool the deployable elements 61 and their surroundings. Cooling may also be provided by the interaction of an electromagnetic field with a gas, liquid, solid or a mixture of any of the preceding. Other cooling means could include the use of chemical or biological endothermic reactions induced by mixing one or more solids and/or one or more liquids. In addition, a separate cooled probe may be provided such that its temperature in combination with selected temperatures for each deployable element provide the desired thermal field. All means for cooling the deployable elements 61 are encompassed herein by the term "heat sink." The thermal treatment of the tissue may occur by the thermal conduction of heat from the individual elements or may be from high temperature solids, liquids, gases or mixtures of the preceding injected from the deployable elements or the tip into the target tissue. Injection may be accomplished as described below with respect to the injection of additives to alter the thermal properties of the tissue.

The temperature of the deployable elements 61 may be monitored by thermal sensors at the ends of the elements. The thermal sensors may be miniature thermocouples 62 located within the end of each element 61. The temperatures may be monitored and controlled by a data processing device, such as a microprocessor 63.

In a further alternative embodiment, the tip 60 is provided with a plurality of deployable elements 61 that are individually deployable to various shapes. The deployable elements remain retracted in the tip during insertion into the tissue to be treated. The tip 60 may be heated by joule heating using a miniature heating coil and/or the individual elements may be heated separately. Each element 61 is individually connected to means for deploying the elements. The deploying means may a direct mechanical connection from the thermal conductive elements 61 to an external mechanical control 64 or the deploying means may be associated with each individual deployable element 61 as described below. Other techniques to deploy the elements 61 to a specified shape would be known to those skilled in the art. These techniques could include electromechanical or pneumatic means. Other techniques could include the application of temperature to induce a shape change in bimetallic elements. Over- or under-treatment of the tissue may be avoided by deploying the deployable conductive elements 61 to individually controllable shapes to generate a thermal field 70 that approximates the shape of the spatial volume of the tissue to treated. As shown in the example of FIG. 15B, the thermal field 70 is generated by elements 61 having the same extended shape and element 81 having a shorter extended shape. The deployable elements themselves may comprise sub-elements or materials that deploy to form various shapes.

Each deployable element 61 may include its individual temperature and/or shape controller in a modular package 65. The tip 60 may be connected by a hollow fiber 66 to external control devices, such as a microprocessor 63, mechanical actuator 64, heating and/or cooling fluid supply 67, thermal additive supply 68, and electrical power 69. Each modular package 65 may be connected via control lines 71 through the hollow fiber 66 to the respective external control devices 63, 64, 67, 68, 69.

Any number of deployable elements 61 could be used depending upon the application. Although the present invention is not limited thereto, it has been found that eight (8) deployable elements 61 allow the creation of thermal fields 66, 70 that can conform to various shapes of tissue to be treated, for example, spherical, ellipsoidal or oblong. Various sizes and shapes of the tip 60 and the deployable elements 61 as described herein may be used to fit various shapes of tissue to be treated. The tip 60 and the deployable elements 61 may be replaceable and disposable.

Further selectivity in defining the area of tissue to be treated may be achieved by introducing into the tissue thermal additives that alter the thermal properties, such as thermal diffusivity, specific heat capacity, density or thermal conductivity, of the tissue. Such additives are known to those skilled in the art and may include carbon particles (1 nm to 5000 μm) and metal particles including gold nano-particles. Various chemicals are known in the art that bind selectively to tumor cells or that otherwise accumulate in tumors and that can alter the thermal properties of the tumor. It is also known that glucose will increase the thermal conductivity of a tumor into which it is introduced. Any particles, solutions containing particles, metals, ceramics, composites, polymers, organic and inorganic chemicals, solids, liquids, gases and mixtures of the preceding that alter the thermal properties of the tissue (either normal or abnormal tissue) are considered to be additives as encompassed within the scope of the present invention.

The thermal additives may be introduced to the tissue to be treated by various means, for example, by intralesional injection or by intravenous injection. More generally, the present invention encompasses the introduction of additives by an external applicator. The thermal additives may also be introduced systemically to change or affect the properties of the target tissue and boundary in order to make the target tissue more susceptible to thermal treatment. Further, the deployable elements may be employed to spray such additives onto the tissue during or before treatment. A hollow duct 72 in the deployable element 61 may be connected through control lines 71 in the hollow fiber 66 to a source of the additive 68. The additive is than sprayed from one or more ports 73 opening into the hollow duct 72.

The present invention has been described with reference to certain preferred and alternative embodiments that are intended to be exemplary only and not limiting to the full scope of the present invention as set forth in the appended claims.

What is claimed is:

1. An apparatus for the thermal treatment of tissues, comprising:
   a tip;
   a plurality of deployable elements operatively connected to said tip; and
   fluid means associated with each element of said plurality of deployable elements for providing an individually controllable temperature, wherein at least one of said plurality of deployable elements is cooled by said fluid means and at least one of said plurality of deployable elements is heated by said fluid means to a temperature effective to ablate tissue.

2. The apparatus of claim 1, further comprising deployment providing means associated with each element of said plurality of deployable elements for deploying said each element to an individually controllable shape.

3. The apparatus of claim 1, wherein said deployable elements comprise means for applying additives that change the thermal properties of the tissue.

4. The apparatus or claim 3, wherein said additives comprise particles, solutions containing particles, metals, ceramics, composites, polymers, organic and inorganic chemicals, and mixtures of any of the preceding.

5. The apparatus of claim 1, wherein said fluid means is either a gas or a liquid.

6. The apparatus of claim 1, wherein said tip is spherical-shaped and said plurality of deployable elements are positioned around a perimeter of said tip.

7. A method for the thermal treatment of tissue, comprising the steps of
   (a) determining a spatial shape of a volume of tissue to be treated;
   (b) providing a tip having a plurality of deployable elements comprising fluid means associated with each element of said plurality of deployable elements for providing an individually controllable temperature;
   (c) selecting a temperature for each element whereby a thermal field is generated having a shape selected to treat the spatial shape of the volume of tissue;
   (d) positioning the tip into the volume of tissue to be treated;
   (e) generating the temperature selected for each element, wherein at least one of said plurality of deployable elements is heated by said fluid means to a temperature effective to ablate tissue, wherein at least one of said plurality of deployable elements is cooled by said fluid means;
   (f) maintaining the tip in the tissue for a sufficient period of time for said at least one heated deployable thermal conductive element to ablate the tissue; and
   (g) removing the tip from the tissue.

8. The method of claim 7, further comprising applying additives to the tissue, wherein said additives comprise particles, solutions containing particles, metals, ceramics, composites, polymers, organic and inorganic chemicals, and mixtures of any of the preceding.

9. The method of claim 8, wherein said step of applying additives comprises introducing said additives by an external applicator.

10. The method of claim 8, wherein said step of applying additives comprises introducing said additives systemically.

11. The method of claim 7, wherein said tip further comprises deployment providing means associated with each of said elements for deploying each of said elements to an individually predetermined shape.

12. The apparatus of claim 7, wherein said tip is spherical-shaped and said plurality of deployable elements are positioned around a perimeter of said tip.

13. An apparatus for the thermal treatment of tissues, comprising:
   a tip, wherein said tip is spherical-shaped;
   a first deployable element operatively connected to said tip, wherein said first deployable element has an exterior surface and a hollow interior portion, wherein said exterior surface of said first deployable element is heated by a heated fluid in said hollow interior portion of said first deployable element; and
   a second deployable element operatively connected to said tip, wherein said second deployable element has an exterior surface and a hollow interior portion, wherein said exterior surface of said second deployable element is cooled by a chilled fluid in said interior portion of said second deployable element, wherein said first deployable element and said second deployable element are positioned around a perimeter of said tip.

14. The apparatus of claim 13, wherein said first deployable element is operable to apply an additive that changes a thermal property of said surrounding tissue of said first deployable element.

15. The apparatus of claim 14, wherein said additive comprises particles, solutions containing particles, metals, ceramics, compositions, polymers, organic and inorganic chemicals, and mixtures of any of the preceding.

16. The apparatus of claim 13, wherein said first deployable element is deployed to an individually controllable shape.

17. The apparatus of claim 14, wherein said second deployable element is deployed to an individually controlled shape.

18. The apparatus of claim 13, wherein said heated fluid is either a gas or a liquid.

19. The apparatus of claim 13, wherein said chilled fluid is either a gas or a liquid.

* * * * *